(12) United States Patent
Pianca

(10) Patent No.: US 9,199,074 B2
(45) Date of Patent: *Dec. 1, 2015

(54) PERCUTANEOUS IMPLANTATION OF AN ELECTRICAL STIMULATION LEAD FOR STIMULATING DORSAL ROOT GANGLION

(71) Applicant: BOSTON SCIENTIFIC NEUROMODULATION CORPORATION, Valencia, CA (US)

(72) Inventor: Anne Margaret Pianca, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/486,793

(22) Filed: Sep. 15, 2014

(65) Prior Publication Data

US 2015/0005782 A1    Jan. 1, 2015

Related U.S. Application Data

(63) Continuation of application No. 13/900,320, filed on May 22, 2013, now Pat. No. 8,849,422.

(60) Provisional application No. 61/651,815, filed on May 25, 2012.

(51) Int. Cl.
*A61N 1/00* (2006.01)
*A61N 1/05* (2006.01)
*A61B 17/34* (2006.01)

(52) U.S. Cl.
CPC .......... *A61N 1/0553* (2013.01); *A61B 17/3468* (2013.01); *A61N 1/0551* (2013.01); *A61N 1/0558* (2013.01)

(58) Field of Classification Search
CPC ............ A61B 17/3468; A61N 1/0551; A61N 1/0553; A61N 1/0558
See application file for complete search history.

(56) References Cited

U.S. PATENT DOCUMENTS

| 3,918,440 A | 11/1975 | Kraus |
| 5,330,477 A | 7/1994 | Crook |

(Continued)

FOREIGN PATENT DOCUMENTS

| AU | 2012201634 A1 | 4/2012 |
| WO | 03020365 A1 | 3/2003 |

(Continued)

OTHER PUBLICATIONS

Official Communication for U.S. Appl. No. 13/900,320 mailed Mar. 19, 2014.

(Continued)

*Primary Examiner* — George Manuel
(74) *Attorney, Agent, or Firm* — Lowe Graham Jones PLLC; Bruce E. Black

(57) ABSTRACT

A method of implanting an electrical stimulation lead to stimulate a dorsal root ganglion includes providing an electrical stimulation lead having a distal end, a proximal end, a longitudinal length, electrodes disposed along the distal end of the lead, terminals disposed on the proximal end of the body, a plurality of conductors electrically coupling the electrodes to the terminals. The method further includes sequentially inserting a series of hollow introducers into the back of a patient to open a passage to the dorsal root ganglion. Each introducer in the series has an inner diameter larger than an inner diameter of a preceding introducer in the series. The method also includes implanting the electrical stimulation lead through the passage formed using the series of hollow introducers. Upon implantation of the electrical stimulation lead, at least one of the plurality of electrodes is adjacent the dorsal root ganglion.

20 Claims, 12 Drawing Sheets

(56) References Cited

U.S. PATENT DOCUMENTS

| | | |
|---|---|---|
| 5,738,521 A | 4/1998 | Dugot |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 7,993,378 B2 | 8/2011 | Foley et al. |
| 8,175,710 B2 | 5/2012 | He |
| 8,224,450 B2 | 7/2012 | Brase |
| 8,295,944 B2 | 10/2012 | Howard et al. |
| 8,364,278 B2 | 1/2013 | Pianca et al. |
| 8,391,985 B2 | 3/2013 | McDonald |
| 8,768,488 B2 | 7/2014 | Barker |
| 2005/0033374 A1 | 2/2005 | Gerber |
| 2005/0240238 A1 | 10/2005 | Mamo et al. |
| 2007/0150036 A1 | 6/2007 | Anderson |
| 2008/0140152 A1 | 6/2008 | Imran et al. |
| 2008/0140169 A1 | 6/2008 | Imran |
| 2009/0276025 A1* | 11/2009 | Burnes et al. ............. 607/126 |
| 2010/0137938 A1 | 6/2010 | Kishawi et al. |
| 2010/0179562 A1 | 7/2010 | Linker et al. |
| 2010/0241179 A1 | 9/2010 | Gielen et al. |
| 2010/0249875 A1 | 9/2010 | Kishawi et al. |
| 2010/0268298 A1 | 10/2010 | Moffitt et al. |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0101326 A1 | 4/2012 | Simon et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2014/0018885 A1 | 1/2014 | Pianca |

FOREIGN PATENT DOCUMENTS

| | | |
|---|---|---|
| WO | 03084398 A1 | 10/2003 |
| WO | 2005120203 A2 | 12/2005 |
| WO | 2006029257 A2 | 3/2006 |
| WO | 2007041604 A2 | 4/2007 |
| WO | 2010083308 A1 | 7/2010 |

OTHER PUBLICATIONS

International Search Report and Written Opinion mailed Aug. 19, 2013 for PCT/US2013/042268.

* cited by examiner

US 9,199,074 B2

PERCUTANEOUS IMPLANTATION OF AN ELECTRICAL STIMULATION LEAD FOR STIMULATING DORSAL ROOT GANGLION

CROSS-REFERENCE TO RELATED APPLICATIONS

This application is a continuation of U.S. patent application Ser. No. 13/900,320 filed May 22, 2013 which claims the benefit under 35 U.S.C. §119(e) of U.S. Provisional Patent Application Ser. No. 61/651,815 filed on May 25, 2012, which is incorporated herein by reference.

FIELD

The present invention is directed to the area of implantable electrical stimulation systems and methods of making and using the systems. The present invention is also directed to percutaneous implantation of an electrical stimulation lead for stimulation the dorsal root ganglion, as well as electrical stimulation systems containing the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are disposed external to the epidural space. Dorsal root ganglia, however, are disposed in proximity to the spinal cord and the vertebral column.

BRIEF SUMMARY

One embodiment is a method of implanting an electrical stimulation lead to stimulate a dorsal root ganglion. The method includes providing an electrical stimulation lead having a distal end, a proximal end, a longitudinal length, a plurality of electrodes disposed along the distal end of the lead, a plurality of terminals disposed on the proximal end of the body, and a plurality of conductors, each conductor electrically coupling at least one of the electrodes to at least one of the terminals. The method further includes sequentially inserting a series of hollow introducers into the back of a patient to open a passage to the dorsal root ganglion. Each introducer in the series has an inner diameter larger than an inner diameter of a preceding introducer in the series. The method also includes implanting the electrical stimulation lead through the passage formed using the series of hollow introducers. Upon implantation of the electrical stimulation lead, at least one of the plurality of electrodes is adjacent the dorsal root ganglion.

Another embodiment is an electrical stimulation lead implantation kit that includes an electrical stimulation lead having a distal end, a proximal end, a longitudinal length, a plurality of electrodes disposed along the distal end of the lead, a plurality of terminals disposed on the proximal end of the body, and a plurality of conductors, each conductor electrically coupling at least one of the electrodes to at least one of the terminals; and a series of hollow introducers configured and arranged for insertion into the back of a patient to open a passage to a dorsal root ganglion. Each introducer in the series has an inner diameter larger than an inner diameter of a preceding introducer in the series.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to percutaneous implantation of an electrical stimulation lead for stimulation the dorsal root ganglion, as well as electrical stimulation systems containing the leads.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,037; 6,741,892; 7,244,150; 7,672,734; 7,761,165; 7,949,395; 7,974,706; 8,175,710; 8,224.450; and 8,364,278; and U.S. Patent Application Publication. No. 2007/0150036, all of which are incorporated by reference.

Figure 1:
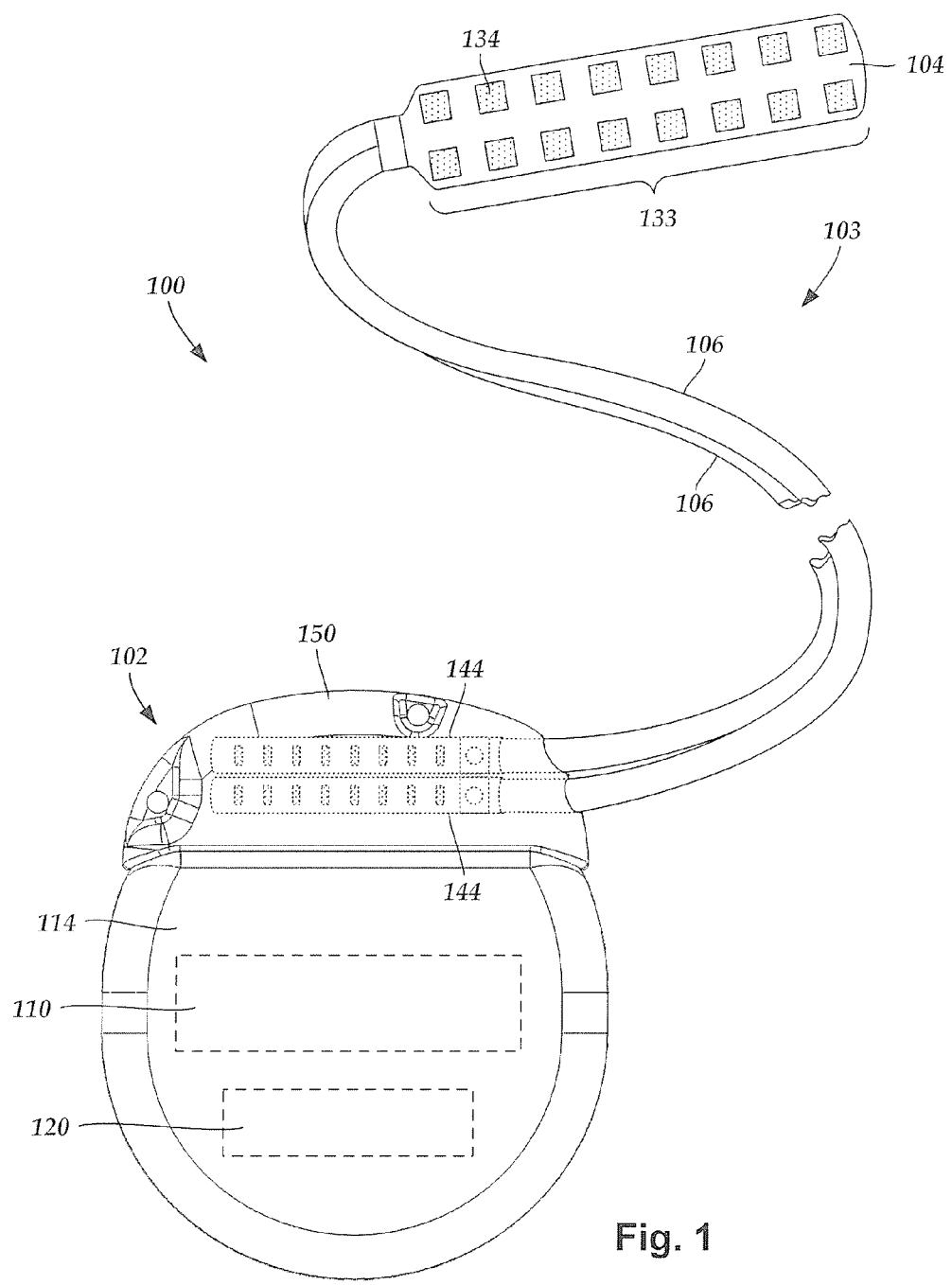
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
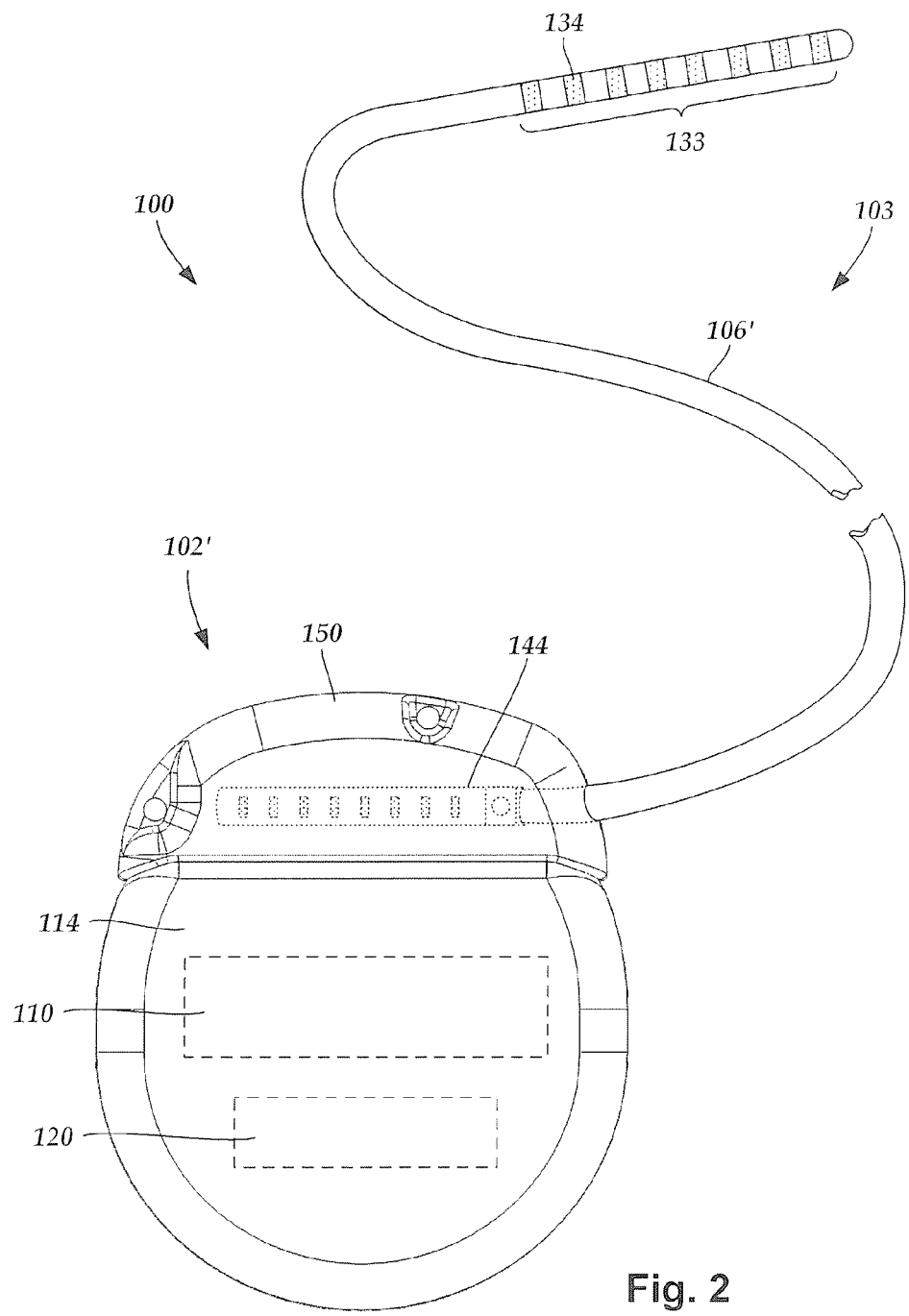
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106'. The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

Any suitable type of electrodes can be used. For example, for lead 103 of FIG. 2, each of the electrodes can be, for example, a ring electrode, a segmented electrode, or a tip electrode and the array of electrodes can include any combination of ring electrodes, segmented electrodes, or a tip electrode. Examples of leads with segmented electrodes include U.S. Pat. Nos. 8,295,944; and 8,391,985; and U.S. Patent Applications Publication Nos. 2010/0268298; 2011/0005069; 2011/0078900; 2011/0130817; 2011/0130818; 2011/0238129; 2011/0313500; 2012/0016378; 2012/0046710; 2012/0165911; 2012/0197375; 2012/0203316; 2012/0203320; and 2012/0203321 and U.S. Provisional Patent Application Ser. No. 61/651,822, all of which are incorporated herein by reference.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
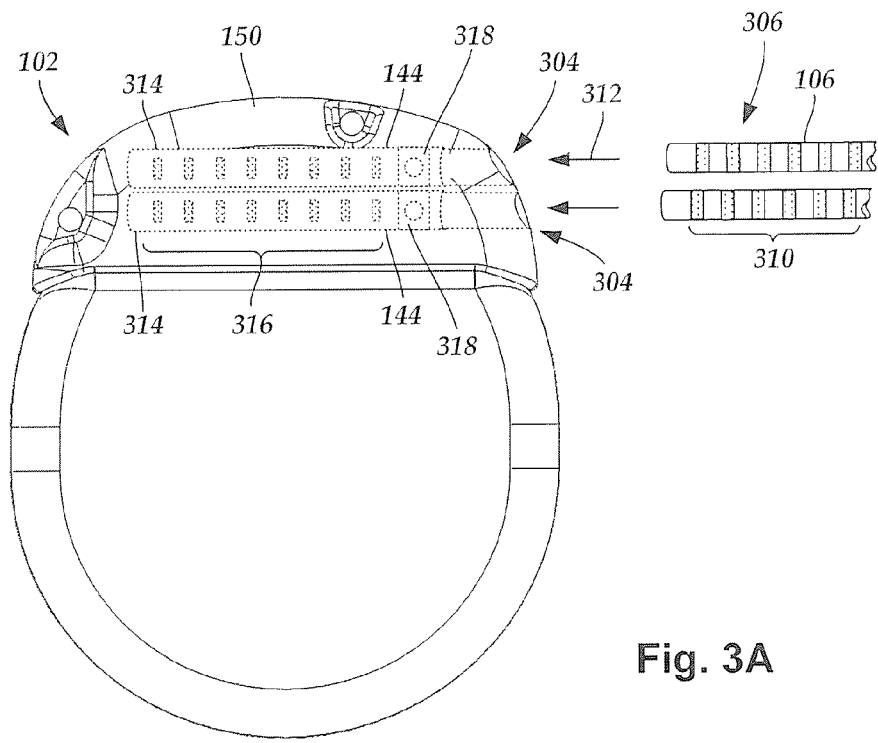
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
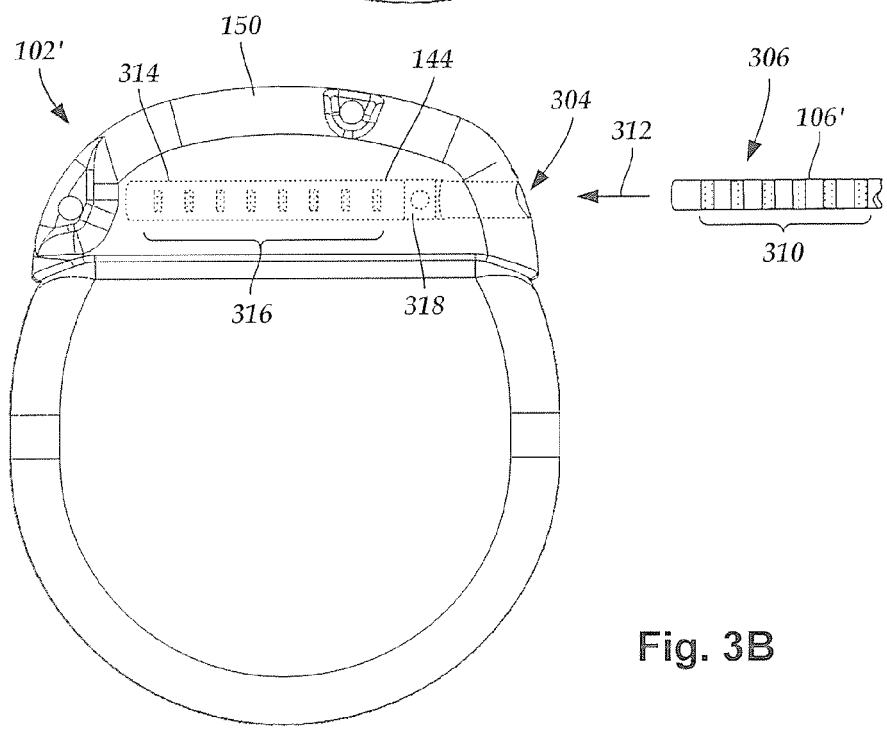
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
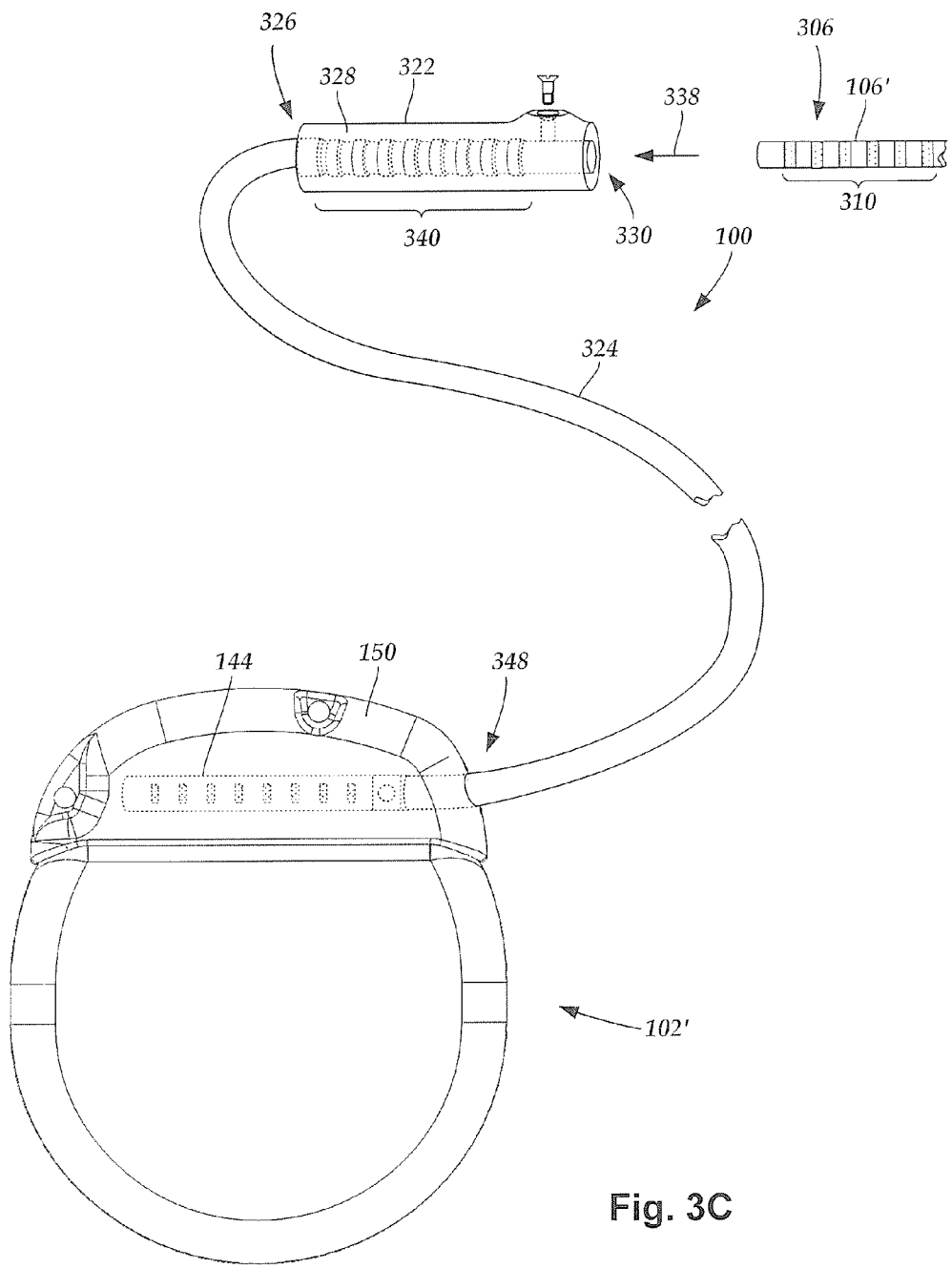
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4A:
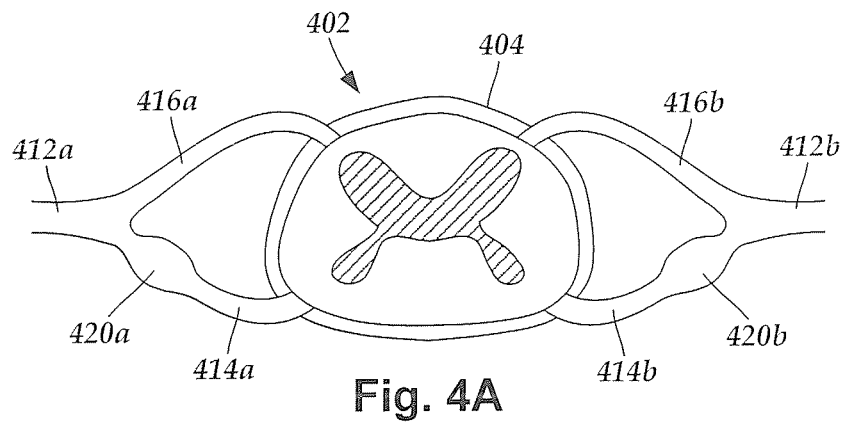
FIG. 4A is a schematic transverse cross-sectional view of spinal nerves extending from a spinal cord, the spinal nerves including dorsal root ganglia.

Turning to FIG. 4A, one potential target stimulation location is the dorsal root ganglia. FIG. 4A schematically illustrates a transverse cross-sectional view of a spinal cord 402 surrounded by dura 404. The spinal cord 402 includes a plurality of levels from which spinal nerves 412a and 412b extend. In at least some spinal cord levels, the spinal nerves 412a and 412b extend bilaterally from the spinal cord 402. In FIG. 4A, the spinal nerves 412a and 412b attach to the spinal cord 402 via corresponding dorsal roots 414a and 414b and corresponding ventral (or anterior) roots 416a and 416b. Typically, the dorsal roots 414a and 414b relay sensory information into the spinal cord 402 and the ventral roots 416a and 416b relay motor information outward from the spinal cord 402. Dorsal root ganglia ("DRG") 420a and 420b are nodules of cell bodies that are disposed along the dorsal roots 416a and 416b in proximity to the spinal cord 402.

Figure 4B:
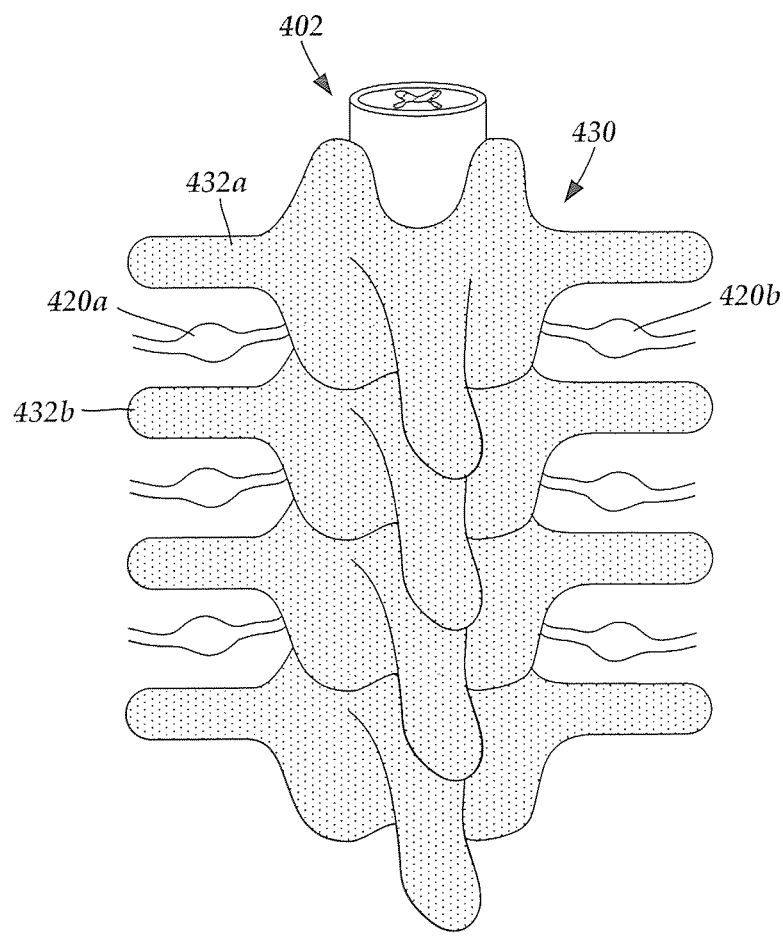
FIG. 4B is a schematic perspective view of a portion of the spinal cord of FIG. 4A disposed in a portion of a vertebral column with the dorsal root ganglia of FIG. 4A extending outward from the vertebral column.

FIG. 4B schematically illustrates a perspective view of a portion of the spinal cord 402 disposed along a portion of a vertebral column 430. The vertebral column 430 includes a plurality of stacked vertebrae, such as vertebrae 432a and 432b, and a plurality of DRGs 420a and 420b extending outwardly bilaterally from the spinal cord 402.

Figure 4C:
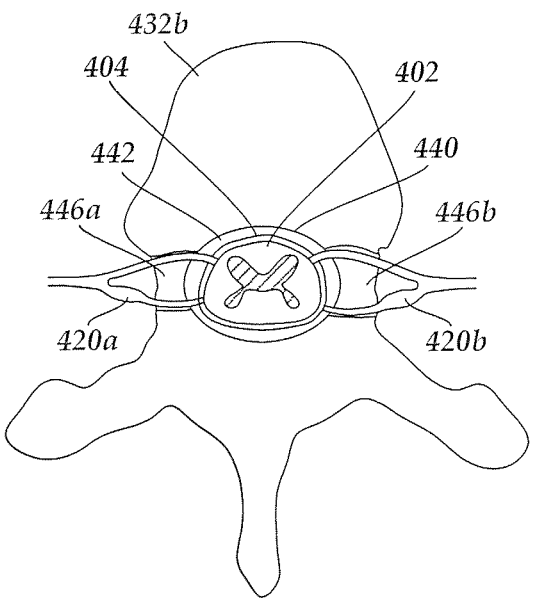
FIG. 4C is a schematic top view of a portion of the spinal cord of FIG. 4A disposed in a vertebral foramen defined in a vertebra of the vertebral column of FIG. 4B, the vertebra also defining intervertebral foramina extending between an outer surface of the vertebra and the vertebral foramen, the intervertebral foramina providing an opening through which the dorsal root ganglia of FIG. 4B can extend outward from the spinal cord of FIG. 4B.

FIG. 4C schematically illustrates a top view of a portion of the spinal cord 402 and dura 404 disposed in a vertebral foramen 440 defined in the vertebra 432b. The vertebrae 432 are stacked together and the vertebral foramina 440 of the vertebrae collectively form a spinal canal through which the spinal cord 402 extends. The space within the spinal canal between the dura 404 and the walls of the vertebral foramen 440 defines the epidural space 442. Intervertebral foramina 446a and 446b defined bilaterally along sides of the vertebra 432b form openings through the vertebra 432b between the epidural space 442 and the environment external to the vertebra 432b.

Figure 4D:
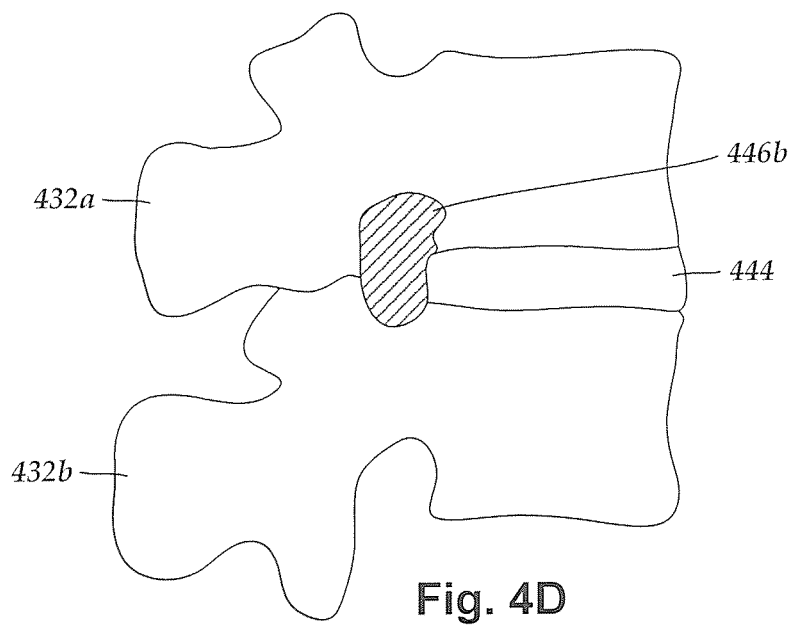
FIG. 4D is a schematic side view of two vertebrae of the vertebral column of FIG. 4B, the vertebrae defining an intervertebral foramen through which the dorsal root ganglia of FIG. 4B can extend outward from the spinal cord of FIG. 4B.

FIG. 4D schematically illustrates a side view of two vertebrae 432a and 432b coupled to one another by a disc 444. In FIG. 4D, the intervertebral foramen 446b is shown defined between the vertebrae 432a and 432b. The intervertebral foramen 446b provides an opening for one or more of the dorsal root 414b, ventral root 416b, and DRG 420b to extend outwardly from the spinal cord 402.

Conventional electrical stimulation leads for spinal stimulation are often implanted into the epidural space and stimulate a portion of the spinal cord. In at some instances, these leads may be implanted percutaneously using an introducer or needle. In other instances, particularly for at least some paddle leads, the lead is implanted using a more invasive procedure, such as a laminectomy.

Instead of stimulating a portion of the spinal cord, an electrical stimulation lead can be used to stimulate the dorsal root ganglion which branches off from the spinal cord. The dorsal root ganglia can be accessed without entry of the lead into the epidural space. Such access, however, may pass through a relatively thick area of tissue, including muscle tissue, to implant the lead. It is desirable to find less invasive methods for implantation of a lead.

The electrical stimulation lead can be implanted near or around the dorsal root ganglion using a set of introducers, each introducer in the set having a larger inner diameter than the preceding introducer. The introducers can be inserted into the patient sequentially starting with the introducer having the smallest inner diameter. This first introducer of the set may be inserted over a guidewire or over or through a needle that has been inserted into patient tissue. Each subsequent introducer is inserted over the preceding introducer so that the opening into the patient becomes sequentially larger. In at least some embodiments, a larger diameter introducer may be inserted deeper into the tissue than the preceding introducer, thereby increasing the depth of the opening, as well as expanding its size.

Once the set of introducers has been inserted into the patient, one or more of smaller diameter introducers (and, in at least some embodiments, all of the introducers except the one with the largest diameter) are removed to leave a passage with access to the dorsal root ganglion and sufficient space to permit a practitioner to reliably implant the distal end of the electrical stimulation lead around or near the dorsal root ganglion. The distal end of the lead is implanted through the passage formed by the introducer(s) and positioned relative to the dorsal root ganglion to be stimulated. The proximal end of the lead can be directed to the site of implantation of the control module. For example, the control module may be implanted in the abdominal cavity and the proximal end of the lead may be directed to the control module by tunneling through the intervening tissue.

Figure 5A:
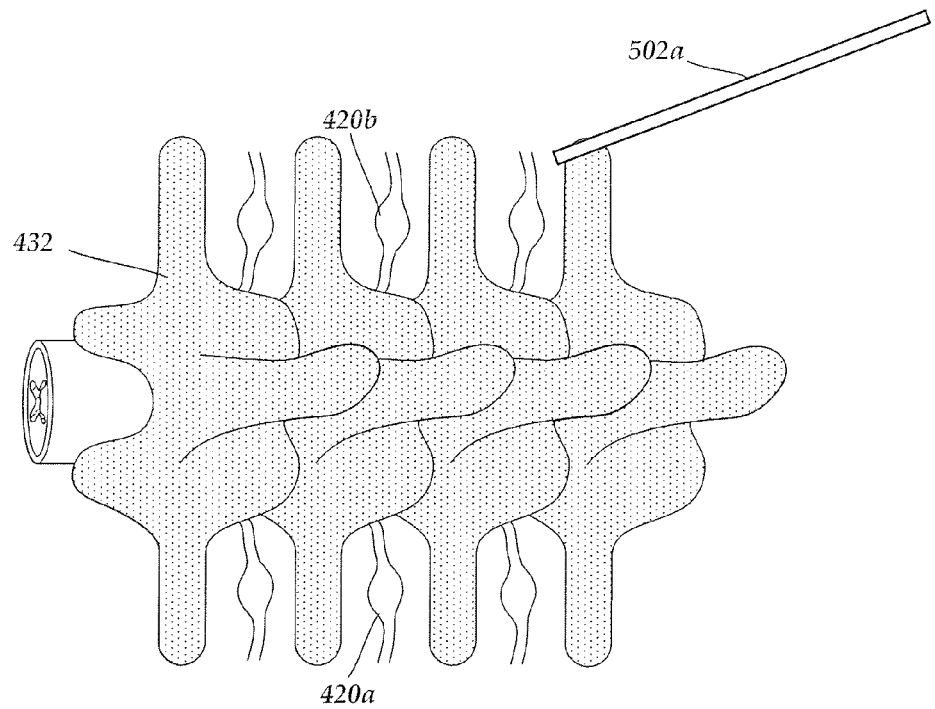
FIG. 5A is a schematic perspective view illustrating the insertion of a first introducer of a series of introducer to obtain access to a dorsal root ganglion for implantation of an electrical stimulation lead, according to the invention.

FIGS. 5A-5E schematically illustrate one embodiment of a method of implanting an electrical stimulation lead using a series of introducers. FIG. 5A illustrates the insertion of a first introducer 502a into patient tissue near the vertebra 432 and directed toward a target dorsal root ganglion 420b. This first introducer 502a may be directed into the tissue without any guiding element or the first introducer may be inserted over a guidewire, needle, or the like (not shown) that had been previously inserted into the tissue. In at least some embodiments, an obturator or trocar is provided within the first introducer to reduce or prevent coring of tissue during insertion of the first introducer.

Figure 5B:
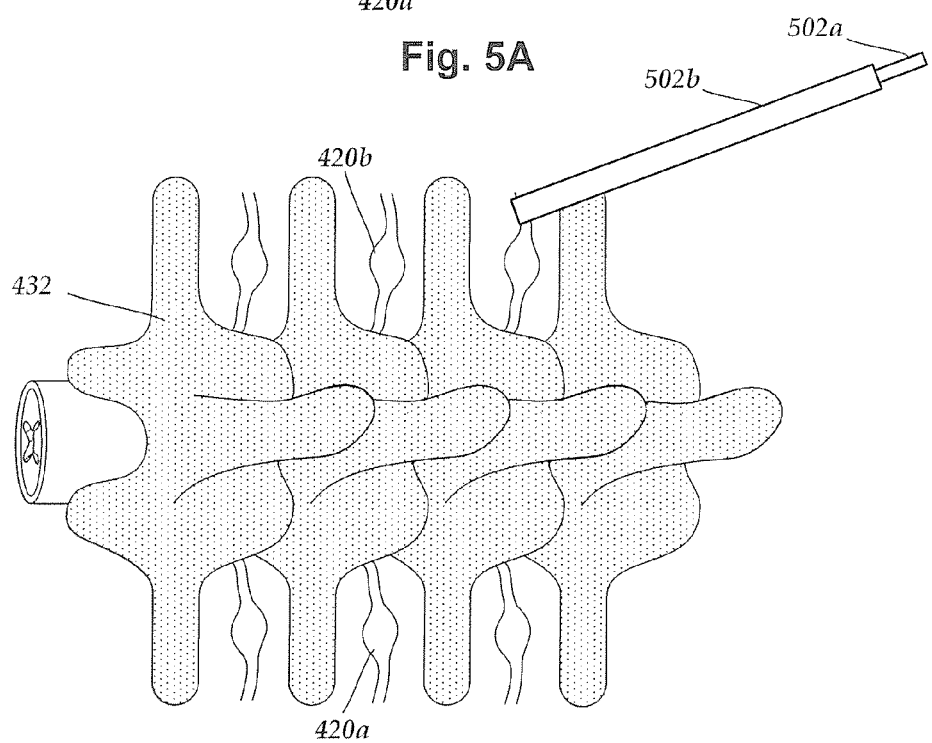
FIG. 5B is a schematic perspective view illustrating the insertion of a second introducer of a series of introducer to obtain access to a dorsal root ganglion for implantation of an electrical stimulation lead, according to the invention.
Figure 5C:
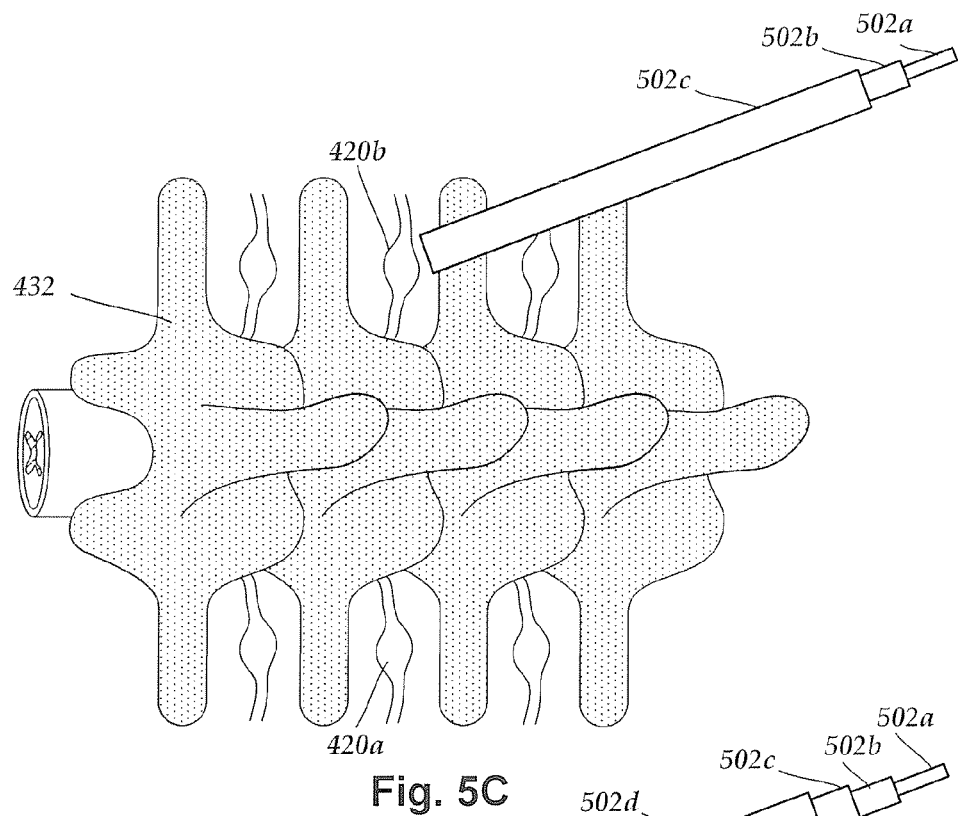
FIG. 5C is a schematic perspective view illustrating the insertion of a third introducer of a series of introducer to obtain access to a dorsal root ganglion for implantation of an electrical stimulation lead, according to the invention.
Figure 5D:
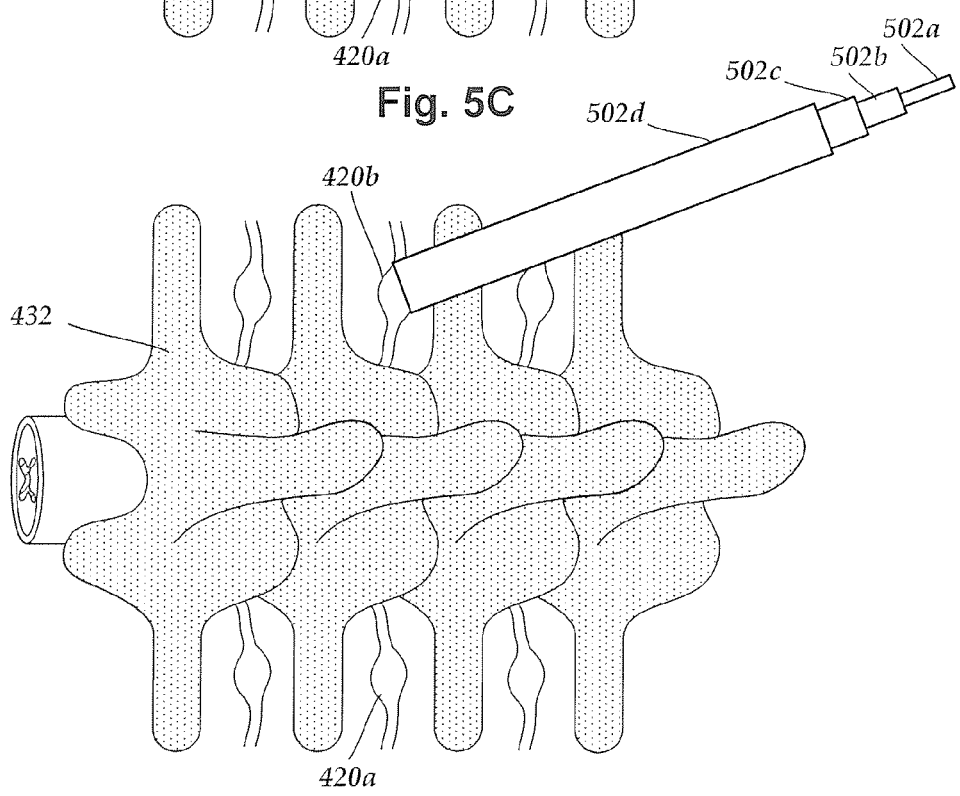
FIG. 5D is a schematic perspective view illustrating the insertion of a fourth introducer of a series of introducer to obtain access to a dorsal root ganglion for implantation of an electrical stimulation lead, according to the invention.

FIG. 5B illustrates the insertion of a second introducer 502b, with a larger inner diameter than the first introducer 502a, over the first introducer 502a. FIG. 5C illustrates the insertion of a third introducer 502c, with a larger inner diameter than the second introducer 502b, over the second introducer 502b. FIG. 5D illustrates the insertion of a fourth introducer 502d, with a larger inner diameter than the third introducer 502c, over the third introducer 502c. In the Figures, each subsequent introducer is pushed closer to the target dorsal root ganglion 420b. In other embodiments, the introducers may be inserted to identical, or near identical, depth in the vicinity of the target DRG. Any number of introducers can be used including, but not limited to, two, three, four, five, six, eight, or more. Typically, but not necessarily, the inner diameter of an introducer is larger than the outer diameter of the preceding introducer(s). Preferably, the introducers slide over each other. In at least some embodiments, a lubricating substance may be used to facilitate sliding of an introducer over the preceding introducer in the series.

Figure 5E:
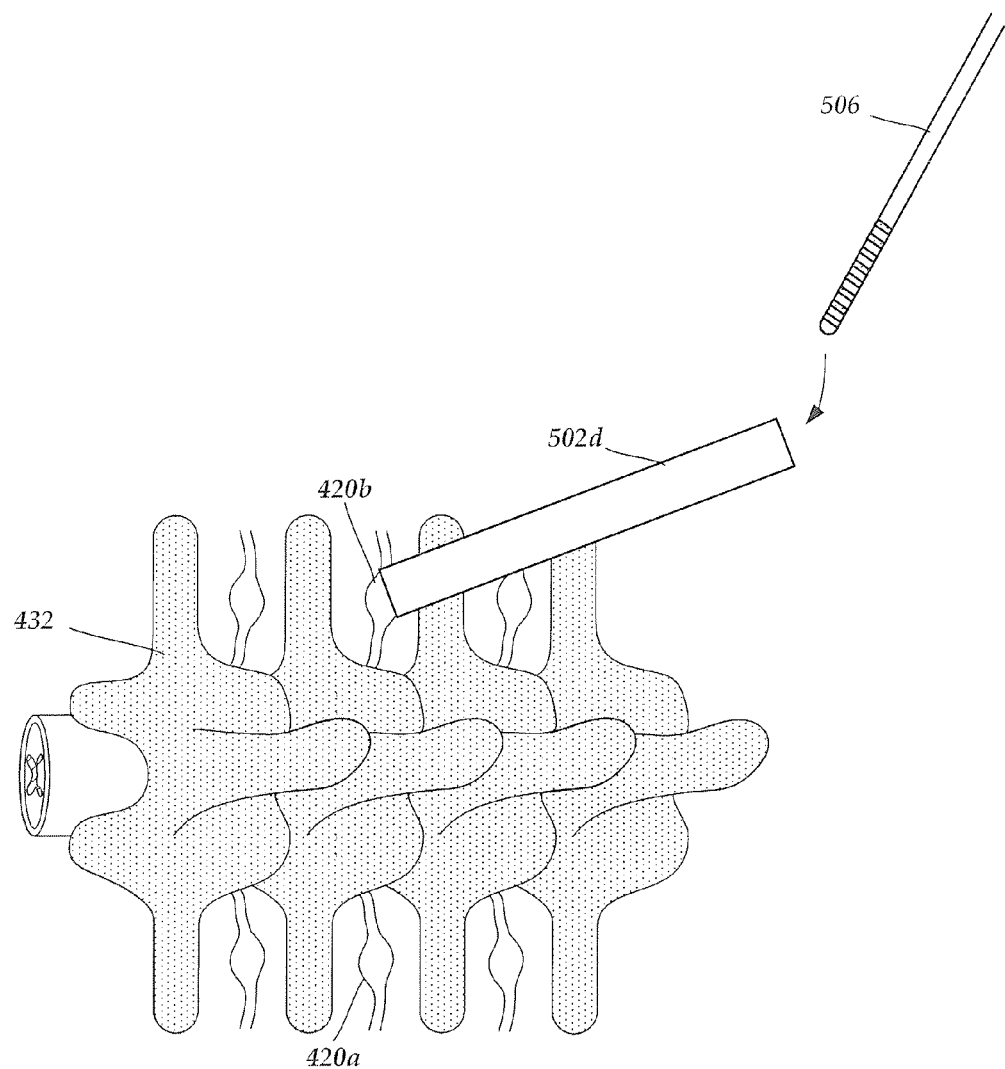
FIG. 5E is a schematic perspective view illustrating the removal of the first, second and third introducers of the series of introducer and the implantation of an electrical stimulation lead near a dorsal root ganglion, according to the invention.

Once the introducers have been inserted, one or more of the earlier introducers are removed. As illustrated in FIG. 5E, the first introducer 502*a*, second introducer 502*h*, and third introducer 502*c* are removed, leaving the fourth introducer 502*d* and a passage defined by the fourth introducer and extending from outside the body to the dorsal root ganglion. In some embodiments, one or more of the preceding introducers may be left within the final introducer to, for example, provide structural stability.

Once the passage is open, an electrical stimulation lead 506 can then be implanted through the passage defined by the introducer 502*d*. The practitioner may select the diameter of the introducer 502*d* and the resulting passage to facilitate the implantation of the lead. Factors that can affect the diameter of the passage include, but are not limited to, the size of the lead, the desired implantation site and arrangement of the lead around the dorsal root ganglion, trauma to the tissue through which the introducer passes, and the like. Similar arrangements of introducers have been developed for spinal surgery including surgery on the vertebrae and discs, as described, for example, in U.S. Pat. No. 7,993,378, incorporated herein by reference, and are instructive for the series of introducers used to implant an electrical stimulation lead as described herein.

Figure 6A:
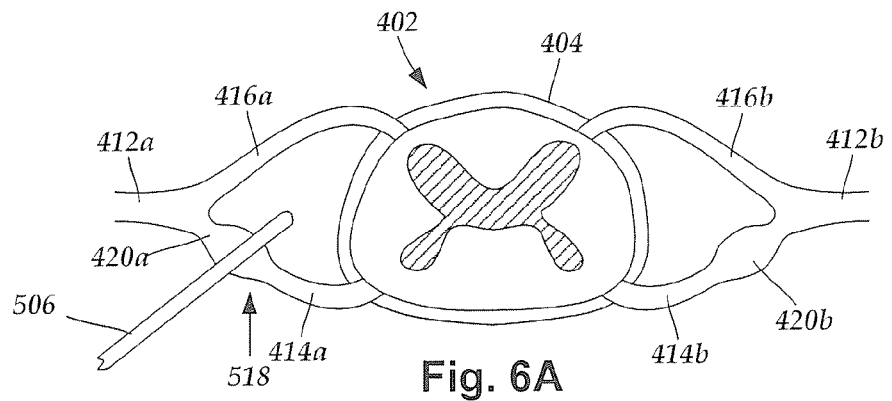
FIG. 6A is a schematic perspective view of one embodiment of a lead implanted near a dorsal root ganglion, according to the invention.

FIGS. 6A-6E illustrate a variety of different implantation arrangements for the distal end 518 of the electrical stimulation lead 506 with respect to the dorsal root ganglion 420*a*. FIG. 6A illustrates one embodiment of a lead 506 with a distal end 518 having a linear or curved shape that lies next to the DRG 420*a*. In these embodiments, the lead forms an angle of at least 45°, 50°, 60°, 70°, 80°, or 85° with the dorsal root 414*a*.

Figure 6B:
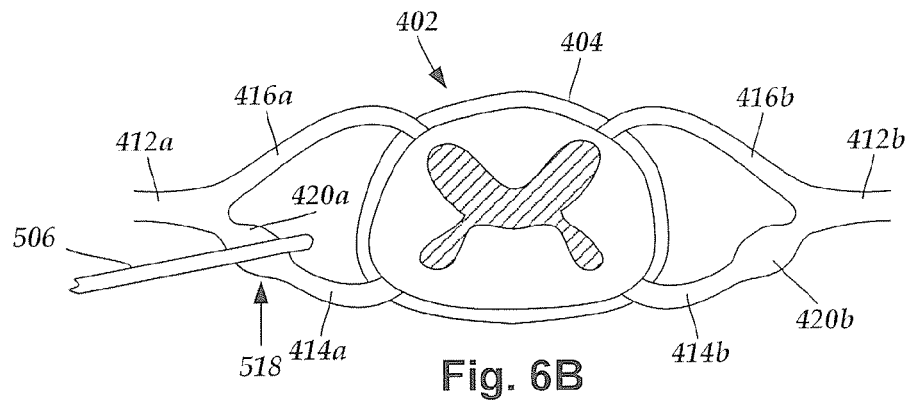
FIG. 6B is a schematic perspective view of a second embodiment of a lead implanted near a dorsal root ganglion, according to the invention.

FIG. 6B illustrates one embodiment of a lead 506 with a distal end 518 having a linear or curved shape that lies next to the DRG 420*a*. In these embodiments, the lead forms an angle of no more than 45°, 30°, 20°, 15°, 10°, or 5° with the dorsal root 414*a*.

Figure 6C:
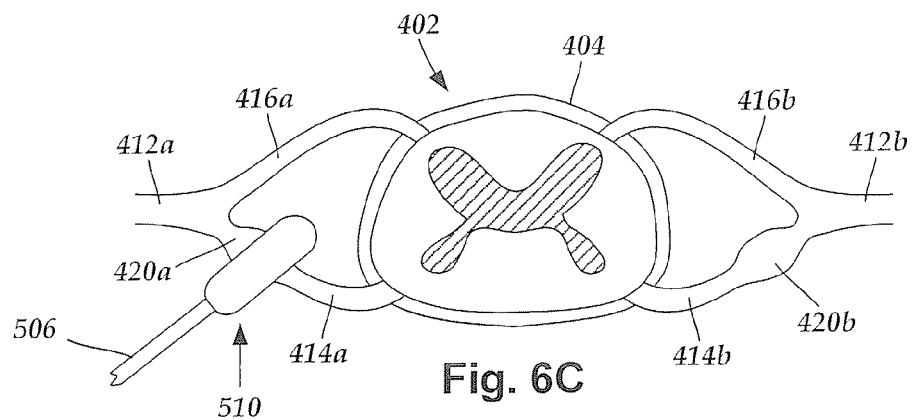
FIG. 6C is a schematic perspective view of one embodiment of a lead having distal end with paddle body implanted near a dorsal root ganglion, according to the invention.

FIG. 6C illustrates one embodiment with a lead 506 with a paddle body 510 at the distal end of the lead. In at least some embodiments, the portion of the lead extending from the paddle body forms an angle of at least 45°, 50°, 60°, 70°, 80°, or 85° with the dorsal root 414*a*, as illustrated in FIG. 6C. In other embodiments, the portion of the lead extending from the paddle body forms an angle of at least 45°, 50°, 60°, 70°, 80°, or 85° with the dorsal root 414*a*

Figure 6D:
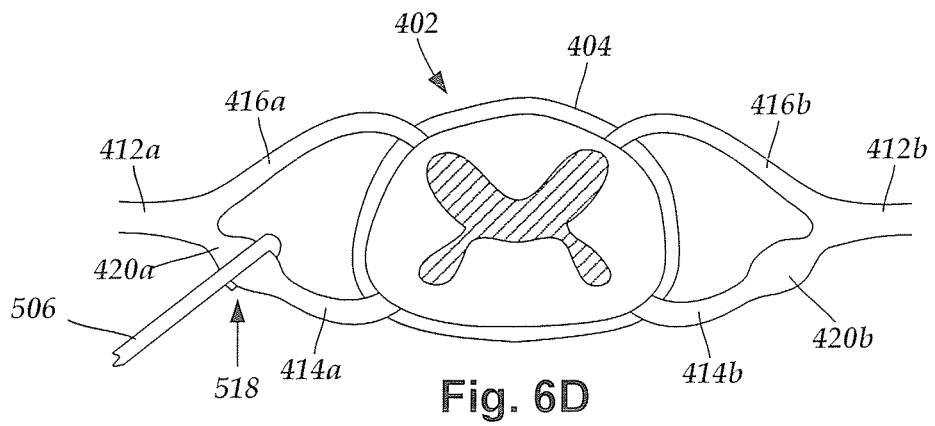
FIG. 6D is a schematic perspective view of one embodiment of a lead having distal end with a hook shape disposed around a dorsal root ganglion, according to the invention.

FIG. 6D illustrates one embodiment of a lead 506 with a distal end 508 of the lead having a hook-shaped distal end 518 to fit around the DRG 420*a*. In at least some embodiments, the hook-shaped distal end extends around at least 40%, 50%, 60%, 70%, 75%, 80%, 90%, 95%, or 100% of the circumference of the DRG 420*a*.

Figure 6E:
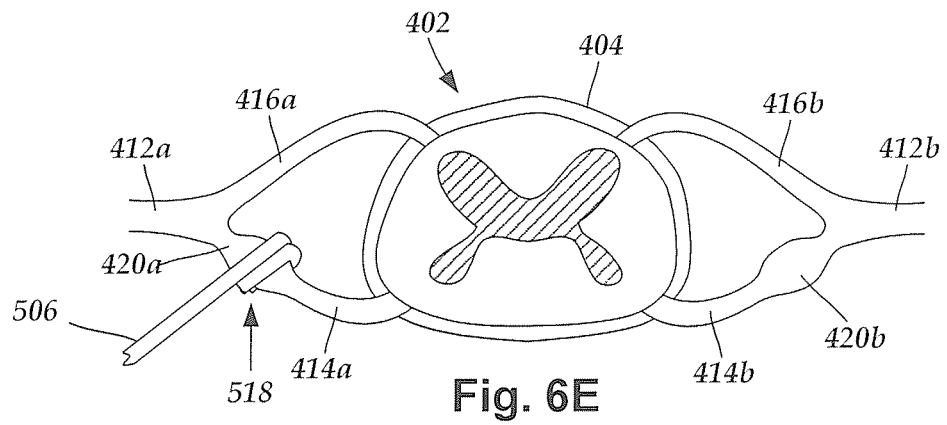
FIG. 6E is a schematic perspective view of one embodiment of a lead having distal end with a coil shape disposed around a dorsal root ganglion, according to the invention.

FIG. 6E illustrates one embodiment of a lead 506 with a distal end 508 of the lead having a coil-shaped distal end 518 to fit around a portion of the DRG 420*a*. The coil-shaped distal end may include any number of full turns (360° turn) around the DRG 420*a* including, for example, at least one, two, or three full turns. The coil-shaped distal end may also include a partial turn (less than 360° turn). The turns of the coil-shaped distal end may be situated immediately adjacent to each other in a touching arrangement, as illustrated in FIG. 6E, or the turns may be separated from each other or any combination thereof.

In at least some embodiments of the arrangements exemplified by FIGS. 6D and 6E, the portion of the lead extending from the hook-shaped or coil-shaped distal end is arranged to form an angle of at least 45°, 50°, 60°, 70°, 80°, or 85° with the dorsal root 414*a*. In at least some embodiments, the hook-shaped or coil-shaped distal end of the lead body is isodiametric. In at least some embodiments, the hook-shaped or coil-shaped distal end of the lead body is also isodiametric with the remainder of the lead. Further description of leads with hook-shaped or coiled-shaped distal end can be found in U.S. Provisional Patent Application Ser. No. 61/651,830, incorporated herein by reference.

Figure 7:
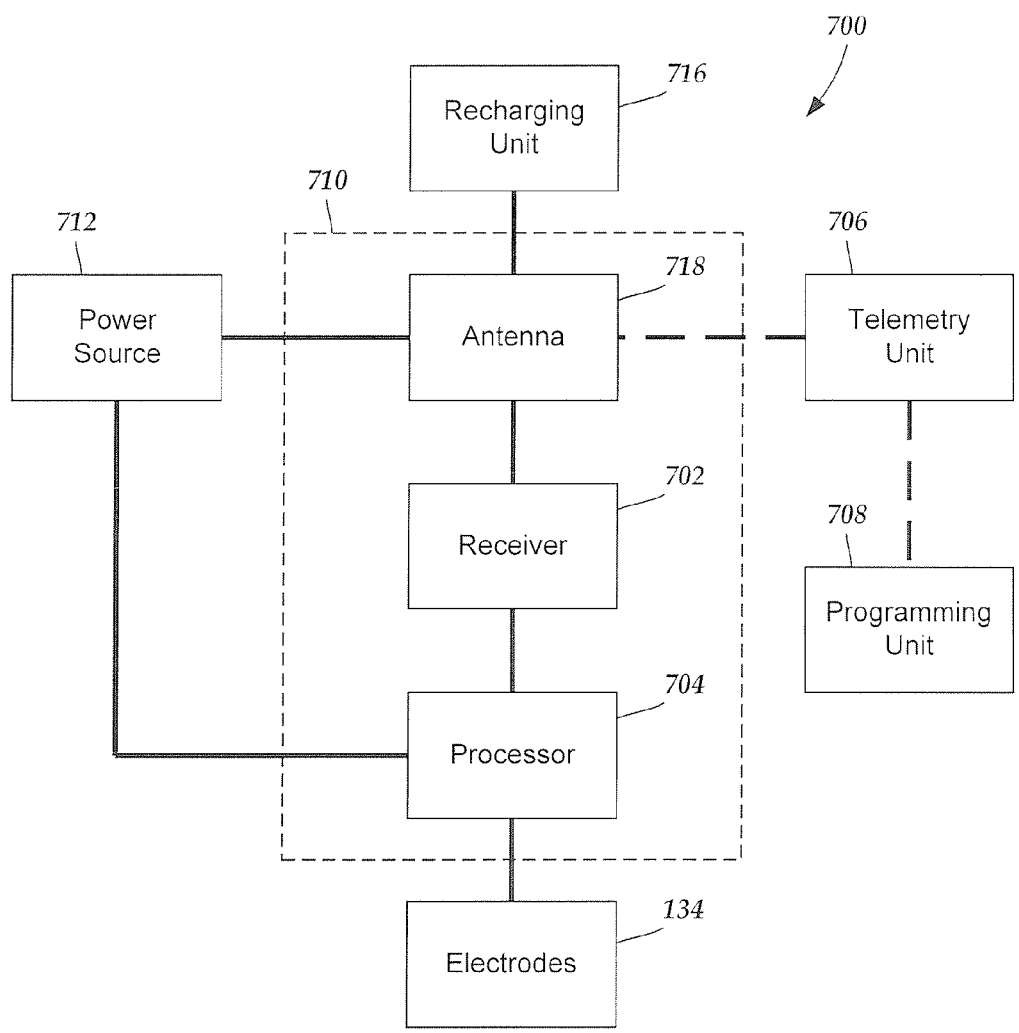
FIG. 7 is a schematic overview of one embodiment of components of an electrical stimulation system, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of implanting an electrical stimulation lead to stimulate a dorsal root ganglion, the method comprising:
   providing an electrical stimulation lead having a distal end, a proximal end, a longitudinal length, a plurality of electrodes disposed along the distal end of the lead, a plurality of terminals disposed on the proximal end of the lead, and a plurality of conductors, each conductor electrically coupling at least one of the electrodes to at least one of the terminals;
   sequentially inserting a series of hollow introducers into a back of a patient to open a passage to the dorsal root ganglion, each introducer in the series sliding over a preceding introducer in the series; and
   implanting the electrical stimulation lead through the passage formed using the series of hollow introducers, wherein, upon implantation of the electrical stimulation lead, at least one of the plurality of electrodes is adjacent the dorsal root ganglion.

2. The method of claim 1, further comprising, prior to implanting the electrical stimulation lead, removing a plurality of the introducers in the series leaving at least a last-inserted introducer in the patient.

3. The method of claim 2, wherein removing a plurality of the introducers comprises removing all of the introducers except the last-inserted introducer.

4. The method of claim 1, wherein the electrical stimulation lead is an isodiametric lead.

5. The method of claim 1, wherein the electrical stimulation lead further comprises a paddle body disposed at the distal end of the electrical stimulation lead.

6. The method of claim 1, wherein implanting the electrical stimulation lead comprises implanting the lead around at least a portion of the dorsal root ganglion with the distal end of the lead formed into a hook shape situated around the portion of the dorsal root ganglion.

7. The method of claim 1, wherein implanting the electrical stimulation lead comprises implanting the lead around at least a portion of the dorsal root ganglion with the distal end of the lead formed into a coil shape situated around the portion of the dorsal root ganglion.

8. The method of claim 1, wherein implanting the electrical stimulation lead comprises implanting the electrical stimulation lead so that the lead forms an angle of at least 45° with respect to a dorsal root extending from the dorsal root ganglion.

9. The method of claim 1, wherein implanting the electrical stimulation lead comprises implanting the electrical stimulation lead so that the lead forms an angle of no more than 25° with respect to a dorsal root extending from the dorsal root ganglion.

10. An electrical stimulation lead implantation kit, comprising:
    an electrical stimulation lead having a distal end, a proximal end, a longitudinal length, a plurality of electrodes disposed along the distal end of the lead, a plurality of terminals disposed on the proximal end of the lead, and a plurality of conductors, each conductor electrically coupling at least one of the electrodes to at least one of the terminals, wherein the distal end of the electrical stimulation lead is formed in a hook or coil shape; and
    a series of hollow introducers configured and arranged for insertion into a back of a patient to open a passage to a dorsal root ganglion, each introducer in the series configured and arranged to slide over a preceding introducer in the series.

11. The electrical stimulation lead implantation kit of claim 10, wherein the electrical stimulation lead is an isodiametric lead.

12. The electrical stimulation lead implantation kit of claim 10, further comprising a control module coupleable to the terminals of the electrical stimulation lead.

13. The electrical stimulation lead implantation kit of claim 10, further comprising a lead extension coupleable to the electrical stimulation lead.

14. A method of implanting an electrical stimulation lead, the method comprising:
    providing an electrical stimulation lead having a distal end, a proximal end, a longitudinal length, a plurality of electrodes disposed along the distal end of the lead, a plurality of terminals disposed on the proximal end of the lead, and a plurality of conductors, each conductor electrically coupling at least one of the electrodes to at least one of the terminals, wherein the distal end of the electrical stimulation lead is formed in a hook or coil shape;

sequentially inserting a series of hollow introducers into a patient to open a passage to an implantation site, each introducer in the series having an inner diameter larger than an inner diameter of a preceding introducer in the series; and implanting the electrical stimulation lead through the passage formed using the series of hollow introducers, wherein, upon implantation of the electrical stimulation lead, at least one of the plurality of electrodes is adjacent to the implantation site.

15. The method of claim 14, further comprising, prior to implanting the electrical stimulation lead, removing a plurality of the introducers in the series leaving at least a last-inserted introducer in the patient.

16. The method of claim 14, wherein sequentially inserting a series of hollow introducers into the patient comprises inserting at least one of the introducers of the series deeper into patient tissue than an immediately preceding one of the introducers was inserted.

17. The method of claim 16, wherein sequentially inserting a series of hollow introducers into the patient comprises inserting each of the introducers of the series deeper into patient tissue than an immediately preceding one of the introducers was inserted.

18. The method of claim 14, wherein sequentially inserting a series of hollow introducers into the patient comprises inserting each of the introducers of the series a substantially identical depth into the patient.

19. The method of claim 14, further comprising inserting a guidewire into the patient prior to sequentially inserting the series of hollow introducers into the patient.

20. The method of claim 19, wherein sequentially inserting a series of hollow introducers into the patient comprises inserting a first introducer of the series of hollow introducers over the guidewire.

* * * * *